United States Patent
Hess et al.

(10) Patent No.: US 11,337,842 B2
(45) Date of Patent: May 24, 2022

(54) JOINT ORTHOSIS WITH MOVABLE PAD

(71) Applicant: Bauerfeind AG, Zeulenroda-Triebes (DE)

(72) Inventors: Heinrich Hess, Kleinblittersdorf (DE); Hans B. Bauerfeind, Zeulenroda-Triebes (DE)

(73) Assignee: BAUERFEIND AG, Zeulenroda-Triebes (DE)

( * ) Notice: Subject to any disclaimer, the term of this patent is extended or adjusted under 35 U.S.C. 154(b) by 319 days.

(21) Appl. No.: 16/634,948

(22) PCT Filed: Jul. 31, 2018

(86) PCT No.: PCT/EP2018/070669
§ 371 (c)(1),
(2) Date: Jan. 29, 2020

(87) PCT Pub. No.: WO2019/025403
PCT Pub. Date: Feb. 7, 2019

(65) Prior Publication Data
US 2020/0206009 A1    Jul. 2, 2020

(30) Foreign Application Priority Data
Aug. 1, 2017  (DE) .................... 10 2017 213 300.7

(51) Int. Cl.
*A61F 5/01*    (2006.01)
(52) U.S. Cl.
CPC .......... *A61F 5/0125* (2013.01); *A61F 5/0193* (2013.01); *A61F 2005/0146* (2013.01); *A61F 2005/0155* (2013.01); *A61F 2005/0158* (2013.01); *A61F 2005/0167* (2013.01); *A61F 2005/0172* (2013.01)

(58) Field of Classification Search
CPC .................. A61F 5/0125; A61F 5/0193; A61F 2005/0146; A61F 2005/0155; A61F 2005/0158; A61F 2005/0167; A61F 2005/0172; A61F 2005/0174;
(Continued)

(56) References Cited

U.S. PATENT DOCUMENTS

| 2012/0289878 A1 | 11/2012 | Schwenn et al. |
| 2013/0296757 A1 | 11/2013 | Kaphingst |
| 2015/0216701 A1* | 8/2015 | Semsch ................. A61F 5/0102 602/26 |

FOREIGN PATENT DOCUMENTS

| DE | 10 2012 218 804 A1 | 4/2014 | |
| DE | 102012218804 A1 * | 4/2014 | ........... A61F 5/0102 |

(Continued)

OTHER PUBLICATIONS

English translation of the Written Opinion from Corresponding International Application No. PCT/EP2018/070669 dated Nov. 23, 2018.

(Continued)

*Primary Examiner* — Tarla R Patel
(74) *Attorney, Agent, or Firm* — Pearne & Gordon LLP

(57) ABSTRACT

The application relates to an active joint orthosis, particularly an orthosis for the hip joint, with an extended therapeutic function and including a joint splint with articulated arms that can be pivoted relative to one another and a pad that can be actively moved via a coupling joint or cam profile on one articulated arm.

9 Claims, 4 Drawing Sheets

Figures 1A, 1B:
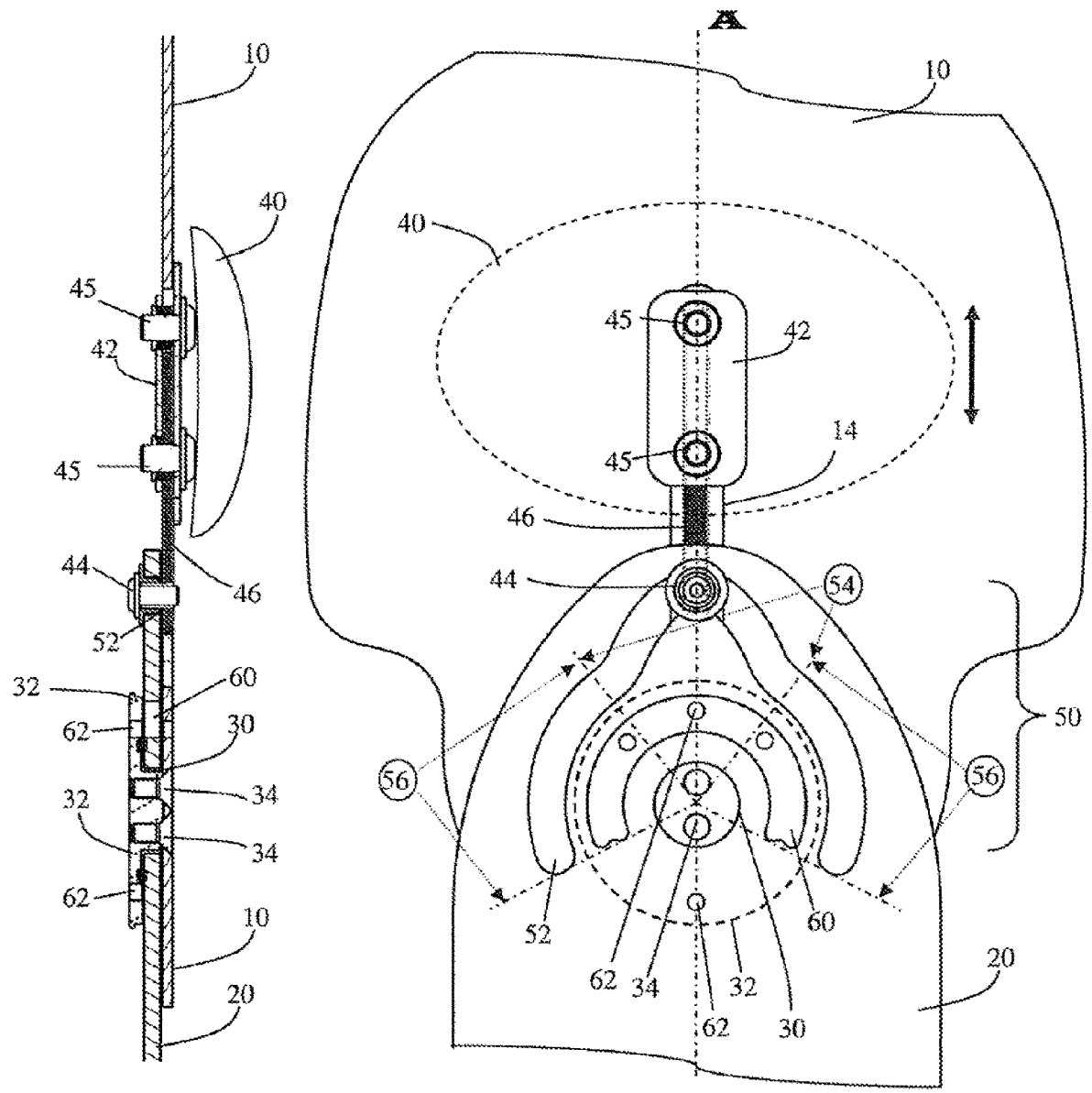

(58) Field of Classification Search
CPC .... A61F 2005/0179; A61F 5/30; A61F 2/605; A61F 2/64; A61F 5/01
See application file for complete search history.

(56) References Cited

FOREIGN PATENT DOCUMENTS

WO    2005/099638 A1    10/2005
WO    WO-2011066323 A1 *  6/2011  ........... A61F 5/0193

OTHER PUBLICATIONS

International Preliminary Report on Patentability for corresponding International Application No. PCT/EP2018/070669 dated Feb. 4, 2020.
International Search Report from Corresponding International Application No. PCT/EP2018/070669 dated Nov. 23, 2018.
Written Opinion from Corresponding International Application No. PCT/EP2018/070669 dated Nov. 23, 2018.

* cited by examiner

JOINT ORTHOSIS WITH MOVABLE PAD

FIELD OF THE INVENTION

The invention relates to an active joint orthosis, particularly an orthosis for the hip joint, with extended therapeutic function provided by an articulated splint with an actively moving pad.

BACKGROUND OF THE INVENTION

Cross-joint joint orthoses for supporting or guiding movement of a body joint are known in the art. These typically comprise a frame above the body joint to be supported and a frame below it. These frames are connected via at least one articulated splint. The articulation axis of the articulated splint is positioned in the region of the body joint. Due to the articulated coupling of the lower and the upper frame, the joint orthosis is guided together with the joint when the joint is flexed or extended, enabling the orthosis to support or guide the joint movement.

Joint orthoses for the hip joint should be suitable, for example, for treating hip arthrosis or coxarthrosis and should relieve pressure on the hip joint. In a hip orthosis, the upper frame (hip part) is formed first by a pelvic harness that firmly encompasses the iliac crest. The upper section or arm of the articulated splint is attached to the pelvic harness. The lower frame encompasses the thigh with straps. The thigh frame is securely attached to the lower section or arm of the articulated splint.

One disadvantage of known joint orthoses is that the mechanically stable construction that is required for the corresponding supporting effect necessitates straps and bandage elements, which reduces the wearing comfort of the orthosis during use. Patient acceptance (compliance) of such orthoses is therefore not always good, especially since the arthrosis to be treated can cause considerable pain with joint movement. This pain occurs in particular because the chronic inflammation caused by osteoarthritis causes the soft tissues of the joint (capsule, etc.) to contract, i.e., to shrink, increasingly restricts mobility, and inevitably makes movements in the joint painful. A very important therapy for expanding range of motion by extending the contracted soft tissues of the joint is, for example, the distal extension treatment performed by physiotherapists by pulling on the leg. This pain relieving pulling could also be modeled using an orthosis. If it were possible to combine wearing the supporting orthosis with simultaneous pain relief, then wearing comfort, compliance, and ultimately the success of the treatment could be improved. Such problems exist especially with hip joints, but also with other arthrotically worn body joints such as knee joints.

BRIEF SUMMARY OF THE INVENTION

It is therefore desirable to provide joint orthoses that have been improved in this manner, which, in addition to a sufficiently supportive or joint-guiding orthotic function, also have a pain-relieving effect on the joints and parts of the body concerned. The technical problem addressed by the present invention was therefore to provide an improved joint orthosis, the wearing comfort and compliance of which are improved.

The technical problem is solved by a novel articulated splint construction, which comprises, on one of the two articulated arms of the articulated splint, an actively movable pad for massaging a part of the body, wherein, when the orthosis is worn and in use, movement of the pad is implemented actively via pivoting of the two articulated arms of the articulated splint relative to one another, i.e., with flexion or extension of the body joint.

For this purpose, the invention provides an orthotic articulated splint according to claim 1 for a joint orthosis. In keeping with this general type of orthosis, the articulated splint has an upper or proximal articulated arm and partially overlapping said arm, a lower or distal articulated arm. The two articulated arms can be pivoted relative to one another, sliding against one another, in at least one articulation axis. The flat upper articulated arm and the flat lower articulated arm have a common articulation axis, which is perpendicular to the surface of the articulated arms. In the region of the articulation axis, the two articulated arms overlap and slide against one another.

According to the invention, a pad carriage, which holds a pad, is provided on the one, in particular upper or proximal articulated arm, and is slidably mounted thereon in a carriage track. According to the invention, the pad carriage is displaceable linearly, particularly rectilinearly, or alternatively along a circular or curved path, relative to the articulated arm that holds it. For this purpose, according to the invention, the pad carriage is coupled in a positively guided manner to the other, in particular lower or distal articulated arm via a motion transmitting mechanism. The motion transmitting mechanism is particularly a cam mechanism or a mechanical linkage; it is generally used to convert a rotational movement, i.e. pivoting, into an angle-dependent translational movement. The actively guided translational movement is predetermined, i.e. programmed, by the dimensions of the gear elements. The rotational movement is produced by the pivoting of the two articulated arms relative to one another; the translational movement is conveyed to the pad carriage, which slides along the carriage track of the upper articulated arm.

In particular, the pad carriage is coupled to the lower articulated arm via the motion transmitting mechanism in such a way that the pivoting of the two articulated arms, particularly during flexion or extension of the body joint, can convey an active displacement of the padded slide on the upper articulated arm. According to the invention, the motion transmitting mechanism converts the pivoting or rotational movement of the two articulated arms to a distal translational movement of the pad.

In the embodiment as a hip joint orthosis, the pad that lies over the trochanter (greater trochanter) exerts downward (distal) momentum on this bone prominence, which leads to extension and improved mobility and thus to relief of pain (physiotherapeutic principle of "extension treatment").

The pad is advantageously connected to the pad carriage and oriented on the articulated splint in such a way that, when the joint orthosis is in place, it is positioned on a part of the body near the body joint, which effects a relief of pain during joint movement. The pad movement is preferably an up and down movement and is actively induced with each extension or flexion of the body joint. Advantageously, the pad is not limited to providing a purely massaging effect, since the actively moving pad in the hip joint orthosis also pulls the extremity itself downward slightly during the relaxed swing phase of the respective leg.

It was unexpectedly found that the actively moving pad noticeably reduces the pain perceived with joint movement, especially in arthritic, contracted, restricted movement joints. In this way, the patient's wearing comfort and compliance of the joint orthosis and thus the success of treatment can be significantly improved. The joint orthosis is no longer perceived as a bothersome technical structure, and is instead accepted as an aid that provides direct pain relief.

A special aspect of the present invention is that the momentum-inducing pad is actively guided positively by the pivoting of the two articulated splint arms relative to one another.

In a preferred configuration, the coupling motion transmitting mechanism is a cam mechanism. This mechanism may be composed in a manner known per se of a cam track along which a follower runs. In a preferred embodiment, the cam mechanism is formed by a flat cam track, in particular, formed on or in the lower articulated arm, and a roller which is positively guided thereon. In a preferred variant of this cam mechanism, the cam track in the lower articulated arm is configured as a slot. The roller travels positively guided in said slot in the manner of a motion link control mechanism.

The roller is coupled to the pad carriage of the upper articulated arm. This is preferably a rigid coupling, in which pad carriage and coupling element, in particular in the form of a push rod, can be configured as integral. In an alternative embodiment, the coupling element is articulated to the pad carriage between the roller and the pad carriage.

To convey the upward and downward movement of the pad on the upper articulated arm, the pad carriage is preferably guided in a carriage track, in particular a straight carriage track, that is oriented substantially radially to the articulation axis of the articulated splint. Said carriage track is formed on or in the upper articulated arm, preferably in the form of a slot. In a variant of this, the pad carriage is guided in a cam track, for example along a circular arc or a serpentine.

In a further alternative embodiment it is provided that the pad carriage is additionally or exclusively rotatably mounted in the upper articulated arm, and the translational movement conveyed by the motion transmitting mechanism is converted to a pure rotational movement of the pad carriage or to a combined rotational and translational movement of the pad carriage, and thus of the pad, on the upper articulated arm.

The cam track is shaped specifically to convey the desired active movement of the pad during joint movement. For this purpose, it is provided in particular that the cam track has at least one slide-active cam section, in addition to at least one slide-neutral cam section. The slide-active section conveys a translational movement of the roller, and thus of the pad carriage, during pivoting of the articulated arms, i.e., during rotational movement. In contrast, a translationally neutral section does not convey a translational movement of the roller, and thus of the pad carriage, during pivoting of the articulated arms, i.e., during rotational movement, because in particular the cam track runs along a circular arc that has a constant radius to the articulation axis.

Preferably it is provided that the movement of the pad is induced particularly when the body joint is relieved of pressure, or alternatively precisely and exclusively at that time. In the hip or knee joint, this is particularly during the movement phase of swinging of the leg when walking, i.e. when the joint is fully extended, corresponding to a 0° joint angle between the two articulated arms. For this purpose, in a preferred embodiment it is provided that the cam track has at least one, or alternatively precisely one, translationally active cam section, above all or alternatively exclusively at the position on the cam track where it can convey a translational deflection of the roller and thus a displacement of the pad carriage in the region of the full extension of the orthotic joint, i.e., at a joint angle of 180°.

In an alternative variant, multiple translationally active cam sections are arranged on the cam track, preferably in the region of full extension of the joint, corresponding to a 0° joint angle between the two articulated arms, and additionally in the region of the two pivot end points, i.e., with full flexion of the joint. In a preferred embodiment thereof, the cam track has three translationally active cam sections. In a further alternative variant, the cam track is configured in a serpentine shape, so that an active movement of the pad is conveyed along the entire pivot range.

In other embodiments of the invention, the motion transmitting mechanism is a mechanical linkage that converts the pivoting, i.e., rotational movement, of the two articulated arms of the articulated splint into the substantially linear translational movement of the pad by means of coupling rods between the lower articulated arm and the pad carriage. In another variant of the invention, a combination of rollers and cables is provided for this conversion of movement according to the invention, the cables being coupled to the lower articulated arm and connected to the pad carriage via rollers which in a preferred embodiment are arranged on the upper articulated arm.

In a special embodiment of the track, the upper articulated arm, in particular, supports at least one pad that is fixed with respect to this articulated splint near the at least one actively movable pad. A combination of actively moving and fixed pad(s) offers an improved efficacy. In a first variant, fixed pads are arranged to the sides of the actively moving pad. In an alternative or additional variant, at least one fixed pad is arranged above the actively moving pad. If the articulated splint is used in a hip orthosis, it is preferably provided that the at least one fixed pad is placed above the hip joint, preferably on the greater trochanter (trochanter major femoris); the actively moving pad is preferably arranged in the region of the gluteal muscles, in particular the gluteus medius and/or gluteus minimus muscles.

The invention also relates to a joint orthosis, preferably a hip joint orthosis or a knee joint orthosis, which contains the orthotic joint splint according to the invention, as described herein. Such a joint orthosis consists at least of an upper frame for the proximal part of the body and a lower frame for the distal part of the body. The two frames are connected via at least one articulated splint according to the invention, and in the case of a knee joint orthosis, preferably via two such articulated splints.

A further aspect of the invention involves the use of the orthotic joint splints according to the invention for prophylaxis and therapy, specifically of arthrosis, in particular in patients suffering from arthrosis. A preferred intended purpose is to improve the wearing comfort and/or the compliance of a joint orthosis, specifically in the context of the aforementioned prophylaxis or therapy.

DESCRIPTION OF EXAMPLE EMBODIMENTS

The invention will be explained in greater detail using the examples described in the following, without being restricted thereto:

FIG. 1A is a schematic diagram showing a plan view of an embodiment of the articulated splint according to the invention. At the base of an upper articulated arm (10), which is configured particularly as an upper shell, an axial joint or articulation axis (30) is provided, which connects this upper articulated arm (10) to a lower articulated arm (20) that overlaps the former, so that the lower articulated arm (20) can be slidingly pivoted in the articulation axis (30) on the upper articulated arm (10). The lower articulated arm

(20) is guided between the upper articulated arm (10) and an articulated plate (32) which is shouldered thereto via bolts (34).

According to the invention, on or in the upper articulated arm (10) a carriage track (14) is formed, in which a pad carriage (42) can slide practically without play. The pad carriage (42) is preferably composed of two plates arranged on the two sides of the flat articulated arm (10) and connected to one another by means of bolts (45). The pad carriage (42) holds at least one preferably cushioned pad (40). In the embodiment depicted, the pad carriage (42) is rigidly connected via a rigid push rod (46) to a roller (44), which travels in the recess of the carriage track (14), parallel thereto. The roller (44) acts as a follower of a cam track (52), which is configured as a flat motion link slot in the pivotable lower articulated arm (20). The roller (44) is guided positively with virtually no play in the motion link with respect to the sliding direction of the pad carriage (42) in the carriage track (14). The cam track (52) that is pivotable about the articulation axis (30) and the guided roller (44) form a cam mechanism (50) according to the invention, which conveys a linear translational/sliding movement of the pad carriage (42) dependent on the pivot angle of the two articulated arms (10, 20) in the axial joint (30).

In the embodiment depicted, the cam track (52) is configured such that translationally neutral cam sections (56) are present in addition to a translationally active cam section (54), arranged here in the center. The translationally neutral cam sections (56) are characterized by being a constant radial distance from the articulation axis (30), so that no lifting movement is conveyed to the roller (44) that travels there. In contrast, the translationally active cam section 56 is configured such that, as soon as the roller (44) enters this section during pivoting, a linear displacement of the guided roller (44) and thus a sliding up or down of the pad carriage (42) in the carriage track (14) is conveyed. In the depicted embodiment, this lifting movement (arrow) takes place in the region of full extension of the joint, i.e., at a joint angle of approximately 0°.

Additionally, the articulated splint is optionally provided with means for limiting pivoting. For this purpose, an arcuate recess (60) is formed in the lower articulated arm (20) within the diameter of the articulation plate (32), which is secured against rotation on the upper articulated arm (10), and one or more holes (62) are provided in the articulation plate (32) for selectively receiving locking pins (not shown). It is provided that these locking pins travel in the recess (60) therebelow and, depending on their positioning, enable a limitation of the pivot angle of the articulated arms (10, 20) relative to one another. The positioning of the holes (62) is shown by way of example. Other positions along the arc (60) are possible.

FIG. 1B shows the embodiment according to FIG. 1 in a longitudinal sectional view along section line A.

Figure 2:
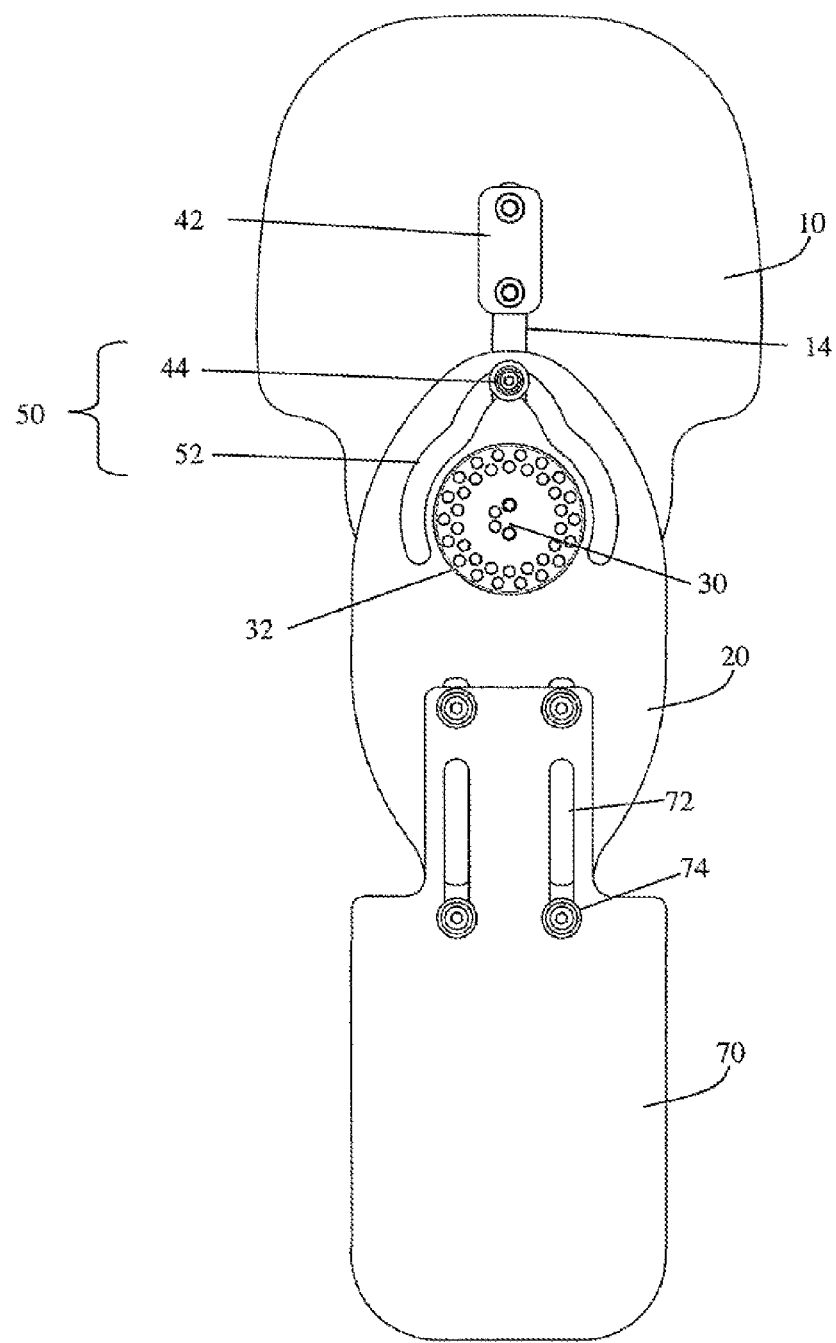

FIG. 2 shows a schematic illustration from a plan view of a variant of the embodiment according to FIGS. 1A and 1B, configured specifically as an articulated track for a hip orthosis. The lower articulated arm (20) supports a track (70) which is adjustable in length via elongated holes (72) and can be fixed to the articulated arm (20) via bolts (74). The pad (40), which can be added to and removed from the pad carriage (42), is attached on the back side and is not shown. The articulation plate (32) has a multiplicity of bored holes (62) for a precisely adjustable limitation of pivoting using locking pins (not shown), which can be inserted into said holes.

Figure 3:
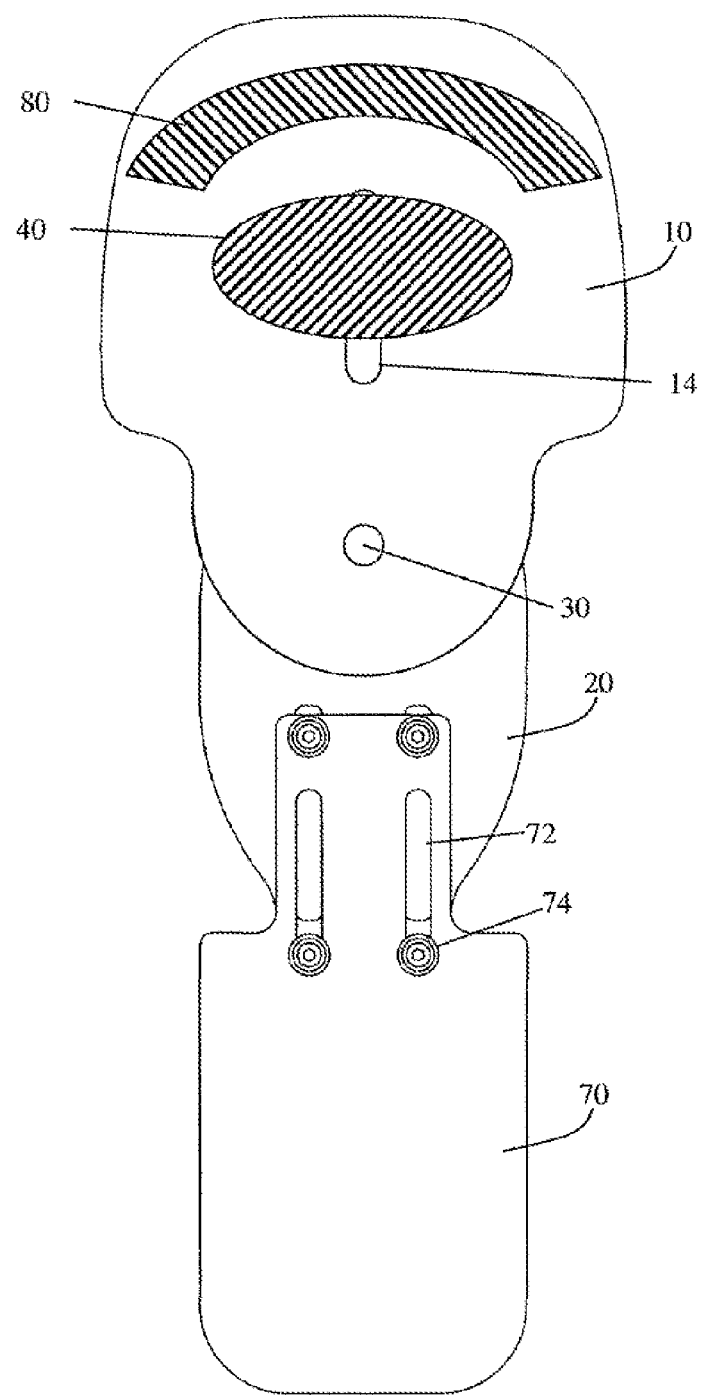

FIG. 3 shows a schematic depiction in a plan view of the reverse side of the embodiment of FIGS. 1A and 1B. The actively movable pad (40) is arranged there and, when the orthosis is in place, faces toward the joint. In the variant shown here, at least one stationary pad (80) fixed to the upper articulated arm (10) is optionally additionally provided.

Figures 4A, 4B:
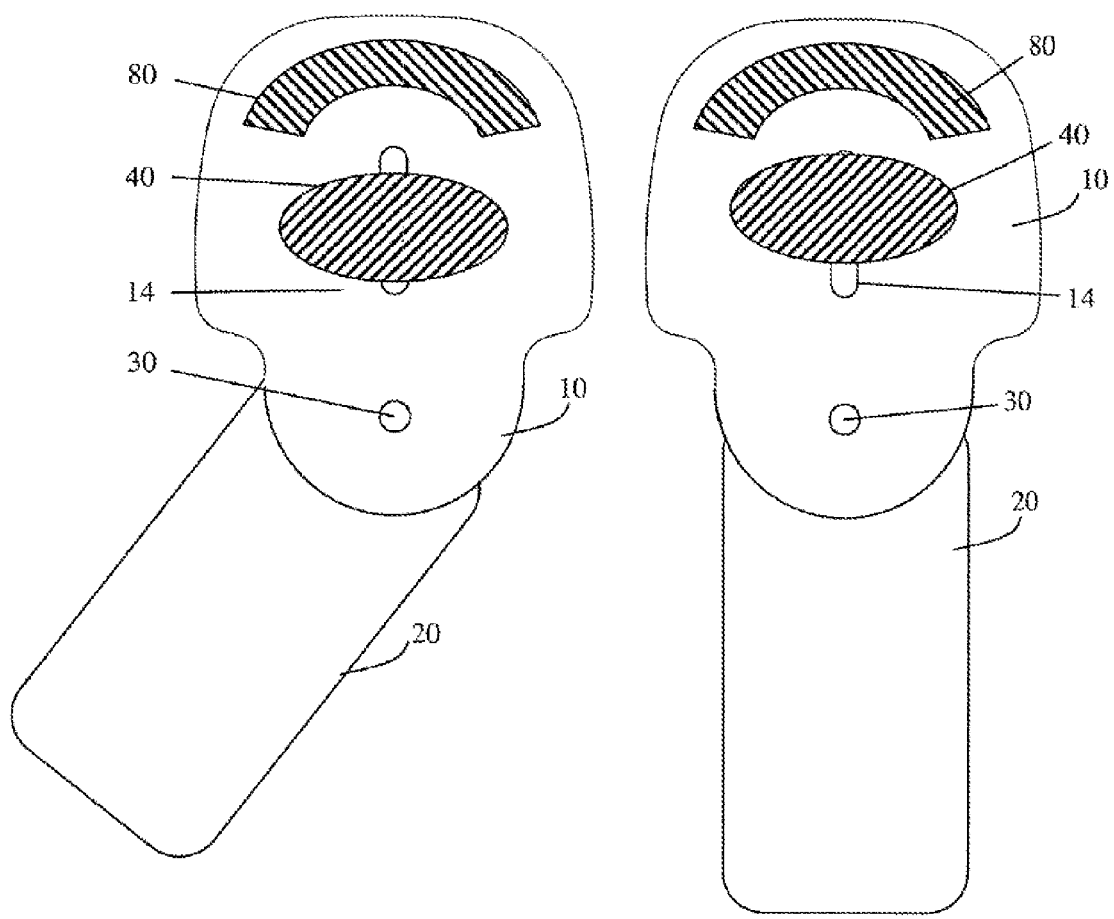

FIGS. 4A and 4B each show, in a schematic depiction of a plan view of the rear side of a variant of the embodiment according to FIG. 3, the functional principle of the articulated splint according to the invention. The actively movable pad (40) is guided via the pad carriage (not shown) in track (14), with the position of the pad being dependent on the pivot angle of the lower articulated arm (20) relative to the upper articulated arm (10) in the articulation axis (30). This angle dependency is conveyed by the motion transmitting mechanism (not shown) according to the invention. FIG. 4A depicts the situation during flexion of the joint. FIG. 4B depicts the situation during extension of joint (joint angle 0°): here, the actively movable pad (40) is shifted actively relative to a stationary position in the direction of the fixed pad (80).

The invention claimed is:

1. An orthotic joint splint having a flat upper articulated arm and a flat lower articulated arm, which is mounted pivotally in an articulation axis perpendicular to said upper articulated arm and which overlaps said arm in the region of the articulation axis, wherein
    on or in the upper articulated arm a pad carriage with a pad is displaceably mounted in a carriage track and the pad carriage is coupled in a positively guided manner to the lower articulated arm via a motion transmitting mechanism, comprising at least one of a cam mechanisms and/or a mechanical linkage wherein the pad carriage is coupled to the lower articulated arm via the motion transmitting mechanism such that the pivoting of the two articulated arms relative to one another can convey a linear displacement of the pad carriage on the upper articulated arm and wherein the motion transmitting mechanism is a cam mechanism composed of a cam track formed on or in the lower articulated arm and a roller that is positively guided therein and is coupled to the pad carriage of the upper articulated arm.

2. The orthotic joint splint according to claim 1, wherein the cam track is configured as a slot in the lower articulated arm.

3. The orthotic joint splint according to claim 1, wherein the cam track has at least one translationally active cam section and at least one translationally neutral cam section.

4. The orthotic joint splint according to claim 3, wherein the cam track has a translationally active cam section that can convey a translational deflection of the roller and the displacement of the pad carriage in the region of full extension of the orthotic joint.

5. The orthotic joint splint according to claim 1, wherein the pad carriage is guided in the carriage track radially to the articulation axis.

6. The orthotic joint splint according to claim 1, comprising at least one additional, fixed pad on the upper articulated arm.

7. A joint orthosis containing the orthotic joint splint according to claim 1.

8. The joint orthosis according to claim 7, comprising at least one of a hip joint orthosis and/or a knee joint orthosis.

9. Use of the orthotic joint splint according to claim 1 to improve the wearing comfort and/or the compliance of a joint orthosis.

\* \* \* \* \*

UNITED STATES PATENT AND TRADEMARK OFFICE
CERTIFICATE OF CORRECTION

| | |
|---|---|
| PATENT NO. | : 11,337,842 B2 |
| APPLICATION NO. | : 16/634948 |
| DATED | : May 24, 2022 |
| INVENTOR(S) | : Heinrich Hess and Hans B. Bauerfeind |

It is certified that error appears in the above-identified patent and that said Letters Patent is hereby corrected as shown below:

In the Specification

Column 5, Line 54, please add -- Figures 1A is a schematic diagram showing a plan of an embodiment of the articulated splint according to the invention --

Signed and Sealed this
Eighteenth Day of April, 2023

Katherine Kelly Vidal
*Director of the United States Patent and Trademark Office*